Sept. 15, 1936. S. HEMMINGS Plant Pat. 193
CARNATION
Filed March 18, 1936
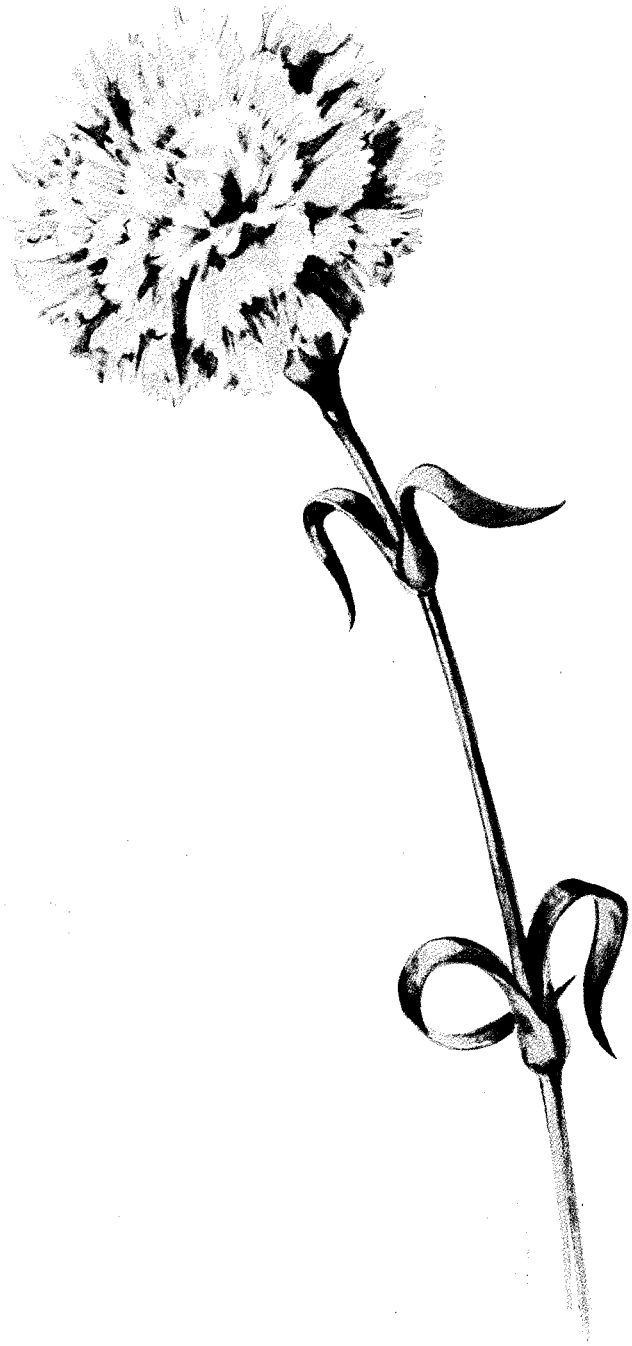
Inventor
SHIRLEY HEMMINGS,
By R. S. Illyn Attorney Patented Sept. 15, 1936

Plant Pat. 193

UNITED STATES PATENT OFFICE

193

CARNATION

Shirley Hemmings, Abington, Mass., assignor to Littlefield-Wyman Nurseries, a copartnership composed of Walton G. Wyman and Lloyd A. Hathaway Application March 18, 1936, Serial No. 69,428

1 Claim. (Cl. 47—60)

The present invention relates to a new variety and strain of carnation, of the type commonly known as perpetual blooming or greenhouse forcing carnation. The novel characteristics of this invention reside particularly in the extremely large size of the bloom, the color unusual for this strain, the robustness of the plant and its toute ensemble.

The present carnation originated as a seedling from Arctic hybridized with the pollen of a seedling of Spectrum itself pollenized with Bernice. The object of these various crosses was to create a carnation of unusual color and at the same time retain the main characteristics of the parent plants, that is their continuity, freeness and profuseness of bloom and usefulness as a greenhouse plant for cut flower purposes. I had in mind the important factor of eliminating the usual tendency of the Spectrum variety to split and breeding in the hardiness and disease resistance qualities of the ancestor Bernice. This involved a long and tedious process of selective hybridization and vegetative propagation with the resultant variety herein described.

Propagation of this new seedling has been accomplished asexually by taking cuttings from the original plant, all of which came true to color. The propagation is in the usual manner of setting cuttings in some good rooting medium until the roots are formed.

The carnation forming the subject matter of this application is considered novel in every particular, as to size, hardiness, the characteristics of the health and foliage of the Bernice variety, the form of the open flower similar to the Arctic variety except being larger and fuller. The color which is very unusual for this strain, the size and shape of the calyx cup, the length and strength of the stem, and unusual robustness of the entire plant are characteristics.

The color of this variety is an especially marked characteristic, shading from a predominating rhodamine purple as shown in plate XII of Ridgway's Color Standards and Color Nomenclature, 1912 edition, to mallow pink of the same plate and edition. Another marked characteristic is the unusual size of the full open flower, often measuring under ordinary good culture four inches in diameter. It is full in the center and gracefully imbricated. The edges of the petals are rather deeply toothed or serrated, and longitudinally curled giving a slightly crinkled appearance.

As a convenient summary the following detailed description of this new variety is given:

Parentage:—

Seedling.

Seed parent—Arctic.

Pollen parent—Unnamed seedling of Bernice x Spectrum.

Classification:—

Botanical, *Dianthus caryophyllus* L. Perpetual flowering carnation.

*Flower*

Blooming habit:—

Recurrent—continuous.

Bud:—

*Size.*—Very large.

*Form.*—Oblong to elliptic obtuse.

*Color.*—When buds first open, mallow pink; when the petals begin to unfold light mallow purple; when half blown inside rhodamine purple shading to mallow pink on the edges. Reverse shading from rhodamine purple to mallow pink as shown on plate XII Ridgway's Color Standards and Color Nomenclature 1912 edition.

*Calyx.*—Shape, campanulate to oblong-campanulate. Size, width at sepals 1½ to 2 cm.; width at base 1 to 1½ cm.; height of calyx cup 2 to 2½ cm. glabrous and slightly glaucous.

*Calyx teeth.*—Short acute to obovate, upright when open. Usually six occasionally five.

*Calyx bracts.*—Four, very broad, abruptly or obtusely pointed.

*Peduncle.*—Length (varies from approximately 8 cm. to 39 cm.); glabrous and glaucous. Color; light green. Strength, firm, erect.

*Opening.*—Opens well, not affected by adverse conditions.

Bloom:—

*Size.*—Very large, average size when fully expanded 8½ cm.; often over 10 cm. in greenhouses.

*Borne.*—Singly.

*Stem.*—Long; in fall approximately 60 cm.; in winter 98 cm.; in spring 122 cm.; strong, holding the flower erect.

*Form.*—A full high center gives it a semi-spherical shape. From a full front view the outer edges of the outer petals form almost a perfect circle.

*Petalage.*—Fifty-six petals under normal conditions.

*Color.*—Shading from mallow pink on outer edges to rhodamine purple predominating on the inside. Reverse of petals shading from mallow purple to mallow pink. General tonality from a distance rhodamine purple. (According to Ridgway, l. c.)

*Variegations.*—None.

*Discoloration.*—General tonality same throughout life of flower.

Petals:—

*Texture.*—Thick, not affected by weather.

*Appearance.*—Inside velvety, outside velvety.

*Form.*—Rather broad spatulate; margins irregularly serrate; longitudinally curled.

*Arrangement.*—Imbricate.

*Center petals.*—Many, small.

*Fragrance.*—Slight.

*Keeping quality.*—On plant very long; as cut flower very long, eight days or more under ordinary conditions.

Sex organs:—

*Stamens.*—Ten or less, white, shorter than ovary, hidden unless exposed by removal of petals.

*Anthers.*—Whitish, very small, mostly sterile.

*Pollen.*—Scarce, creamy white.

*Styles.*—Three or four, white, curved tapering to the apex.

*Stigma.*—Fringed, grooved.

*Ovary.*—More or less ellipsoid, and somewhat lobed, superior, one celled many ovuled.

*Plant*

Form:—

Bush.

Growth:—

Vigorous, branching.

Foliage:—

*Size.*—5–11 mm. wide; 4–12 cm. long.

*Quantity.*—Normal.

*Color.*—Dark green, satiny, growing slightly darker with age.

*Shape.*—Linear, acuminate, clasping stem at base.

*Texture.*—Glabrous, waxy.

*Margin.*—Entire.

*Disease.*—Resistant to fusarium wilt and alternaria blight diseases.

*Stem.*—Long, 60 to 122 cm. depending on season of year. Dark green with grayish bloom. Smooth, firm, and capable of supporting a heavy flower.

The carnation shown and described is claimed by me to be distinguished by the following most important features taken either singly or in combination:

(*a*) The natural color of the blossom is predominantly rhodamine purple.

(*b*) The natural color of the blossom shades from mallow pink on the outer edges to rhodamine purple.

(*c*) The large size and color for the blossoms, their large, full, almost perfect formation, the strong stem of unusual length, the large strong calyx cup, the vigorous growing habits, and freedom from disease are among the important features.

Each of the foregoing features is believed and claimed by me to be new in such type of carnation and in combination they specifically define the new variety.

I claim:

A carnation substantially as described and characterized by a blossom having a predominantly rhodamine purple color.

SHIRLEY HEMMINGS.